(12) United States Patent
Rousmaniere et al.

(10) Patent No.: US 9,996,905 B2
(45) Date of Patent: Jun. 12, 2018

(54) SYSTEMS AND METHODS FOR ENHANCING OBJECT VISIBILITY FOR OVERHEAD IMAGING

(71) Applicant: Planet Labs, Inc., San Francisco, CA (US)

(72) Inventors: Louis Hu Rousmaniere, San Francisco, CA (US); Kenneth James Kryda, Sunnyvale, CA (US)

(73) Assignee: Planet Labs, Inc., San Francisco, CA (US)

( * ) Notice: Subject to any disclaimer, the term of this patent is extended or adjusted under 35 U.S.C. 154(b) by 126 days.

(21) Appl. No.: 15/071,357

(22) Filed: Mar. 16, 2016

(65) Prior Publication Data

US 2017/0270639 A1  Sep. 21, 2017

(51) Int. Cl.
*G06K 9/40* (2006.01)
*G06T 5/00* (2006.01)
(Continued)

(52) U.S. Cl.
CPC ................ *G06T 5/00* (2013.01); *G01C 11/04* (2013.01); *G01N 21/55* (2013.01);
(Continued)

(58) Field of Classification Search
CPC .. G06T 5/00; G06T 7/004; G06T 7/60; G06T 2207/10032
See application file for complete search history.

(56) References Cited

U.S. PATENT DOCUMENTS

| 4,560,279 A | 12/1985 | Kouns |
| 4,688,092 A | 8/1987 | Kamel et al. |

(Continued)

FOREIGN PATENT DOCUMENTS

| CA | 2 798 293 | 6/2013 |
| CN | 103776427 | 5/2014 |

(Continued)

OTHER PUBLICATIONS

Jackson et al., Sandia Report, "On Identifying the Specular Reflection of Sunlight in Earth-Monitoring Satellite Data," On-Orbit Analysis and Support, Sandia National Laboratories, Printed Mar. 2009—30 pages.

(Continued)

*Primary Examiner* — Gregory M Desire
(74) *Attorney, Agent, or Firm* — Dority & Manning, P.A.

(57) ABSTRACT

Systems and methods are provided for enhancing object feature visibility for overhead imaging. In one embodiment, a computing system can obtain information associated with one or more locations of an imaging platform and one or more locations of a solar source. The system can determine one or more positional ranges of the imaging platform relative to the solar source based, at least in part, on such information. The positional ranges can be indicative of positions at which the imaging platform is to obtain image frames depicting at least a portion of a target object. The system can send, to the imaging platform, a set of data indicative of the positional ranges and can receive, from the imaging platform, a set of data indicative of the image frames depicting at least a portion of the target object. The image frames being captured based, at least in part, on the positional ranges.

20 Claims, 9 Drawing Sheets

(51) Int. Cl.
*G06T 7/00* (2017.01)
*G06T 7/60* (2017.01)
*G01C 11/04* (2006.01)
*G01N 21/55* (2014.01)
*G01N 21/956* (2006.01)
*G03B 15/00* (2006.01)
*G06K 9/32* (2006.01)
*H04N 5/232* (2006.01)

(52) U.S. Cl.
CPC ..... *G01N 21/95684* (2013.01); *G03B 15/006* (2013.01); *G06K 9/3241* (2013.01); *G06T 7/004* (2013.01); *G06T 7/60* (2013.01); *H04N 5/232* (2013.01); *G06T 2207/10032* (2013.01)

(56) References Cited

U.S. PATENT DOCUMENTS

| | | | |
|---|---|---|---|
| 5,553,661 A * | 9/1996 | Beyerlein | B60H 1/00735 |
| | | | 165/11.1 |
| 5,686,719 A | 11/1997 | Elkin | |
| 6,433,867 B1 | 8/2002 | Esquivel | |
| 6,921,898 B1 | 7/2005 | Chen | |
| 7,768,631 B1 | 8/2010 | Rovinsk | |
| 8,437,554 B2 * | 5/2013 | Kim | G06T 7/507 |
| | | | 348/135 |
| 9,423,484 B2 * | 8/2016 | Aycock | G01S 3/7861 |
| 9,470,579 B2 * | 10/2016 | Ritter | G01J 3/0297 |
| 2004/0137842 A1 * | 7/2004 | Iwata | H04B 7/18541 |
| | | | 455/12.1 |
| 2006/0046648 A1 * | 3/2006 | DiFonzo | H01Q 1/3275 |
| | | | 455/12.1 |
| 2006/0273965 A1 * | 12/2006 | Gat | H01Q 1/3233 |
| | | | 343/711 |
| 2008/0071431 A1 * | 3/2008 | Dockter | B63B 35/50 |
| | | | 701/3 |
| 2013/0298083 A1 * | 11/2013 | Bertoldo | G06F 3/0482 |
| | | | 715/835 |
| 2014/0022539 A1 * | 1/2014 | France | G01C 15/00 |
| | | | 356/139.1 |
| 2014/0112536 A1 | 4/2014 | Ely et al. | |
| 2016/0037134 A1 * | 2/2016 | Medema | H04N 7/181 |
| | | | 348/135 |

FOREIGN PATENT DOCUMENTS

JP    2011 220964    11/2011
WO   WO 2015/027289    3/2015

OTHER PUBLICATIONS

Sheres, "Remote and Synoptic Water-Wave Measurements by Aerial Photography: A Model, Experimental Results, and an Application," *IEEE Journal of Oceanic Engineering*, vol. OE-6, No. 2, Apr. 1981, pp. 63-69.
PCT International Search Report based off PCT Application No. PCT/US2016/064161, dated Mar. 6, 2017—16 pages.

* cited by examiner

SYSTEMS AND METHODS FOR ENHANCING OBJECT VISIBILITY FOR OVERHEAD IMAGING

FIELD

The present disclosure relates generally to generating images, and more particularly to systems and methods for enhancing object feature visibility for overhead imaging.

BACKGROUND

Scenes captured, for instance, from overhead imaging platforms can include various objects or items. However, details in one region of the scene can be obscured in a shadow, and items of relatively similar color can blend together. Moreover, high light areas of the scene may be saturated, or the low light areas may be too noisy, or both. Accordingly, it can be difficult to distinguish certain details from their surroundings in an image captured from an overhead imaging platform. While higher resolution platforms can be used, they can also increase overall system costs.

SUMMARY

Aspects and advantages of the present disclosure will be set forth in part in the following description, or can be obvious from the description, or can be learned through practice of embodiments of the present disclosure.

One example aspect of the present disclosure is directed to a computing system for enhancing object feature visibility for overhead imaging. The computing system includes one or more processors and one or more memory devices. The one or more memory devices can store computer-readable instructions that when executed by the one or more processors cause the one or more processors to perform operations. The operations can include obtaining a first set of information associated with one or more locations of an imaging platform. The operations can further include obtaining a second set of information associated with one or more locations of a solar source. The operations can include determining one or more positional ranges of the imaging platform relative to the solar source based at least in part on the first and second sets of information. The one or more positional ranges can be indicative of one or more positions at which the imaging platform is to obtain one or more image frames depicting at least a portion of a target object. The one or more positional ranges can be associated with one or more positions of the solar source at which radiation from the solar source causes a higher level of reflectance with the target object than with a surrounding of the target object by creating a specular reflection. The operations can further include sending, to the imaging platform, a first set of data indicative of the one or more positional ranges. The imaging platform can be configured to obtain a second set of data indicative of the one or more image frames depicting at least a portion of the target object based at least in part on the one or more positional ranges. The operations can include receiving, from the imaging platform, a third set of data indicative of one or more of the image frames depicting at least a portion of the target object. The one or more image frames were captured based at least in part on the one or more positional ranges.

Another example aspect of the present disclosure is directed to a computer-implemented method of enhancing object feature visibility for overhead imaging. The method can include obtaining, by one or more computing devices, a first set of information associated with one or more locations of an imaging platform and a second set of information associated with one or more locations of a solar source. The method can further include determining, by the one or more computing devices, one or more positional ranges of the imaging platform relative to the solar source based, at least in part, on the first and second sets of information. The one or more positional ranges can be indicative of one or more positions at which the imaging platform is to obtain data indicative of one or more image frames depicting at least a portion of a target object. The method can include sending, to the imaging platform, a first set of data that is indicative of the one or more positional ranges such that the imaging platform can obtain a second set of data indicative of a plurality of image frames when the imaging platform is within the one or more positional ranges. The method can include receiving, from the imaging platform, a third set of data indicative of one or more of the image frames depicting at least a portion of the target object. The one or more image frames were captured based at least in part on the one or more positional ranges.

Yet another example aspect of the present disclosure is directed to an imaging platform. The imaging platform can include one or more processors and one or more memory devices. The one or more memory devices can store computer-readable instructions that when executed by the one or more processors cause the one or more processors to perform operations. The operations can include receiving a first set of data indicative of one or more image capture conditions. The one or more image capture conditions can be indicative of one or more positional ranges of the imaging platform relative to a solar source. The one or more positional ranges can be associated with one or more positions of the solar source at which radiation from the solar source causes a higher level of reflectance with the target object than with at least one other portion of a region of interest that includes the target object by creating a specular reflection. The operations can further include determining whether a position of the imaging platform is within the one or more positional ranges. The operations can include obtaining a second set of data indicative of a plurality of image frames when the imaging platform is within the one or more positional ranges. Each image frame can depict at least a portion of the region of interest, and one or more of the image frames can depict at least a portion of the target object in the region of interest. The operations can further include sending, to one or more computing devices, a third set of data indicative of at least the one or more image frames that depict at least a portion of the target object.

Other example aspects of the present disclosure are directed to systems, apparatuses, tangible, non-transitory computer-readable media, memory devices, and electronic devices for enhancing object feature visibility for overhead imaging.

These and other features, aspects and advantages of various embodiments will become better understood with reference to the following description and appended claims. The accompanying drawings, which are incorporated in and constitute a part of this specification, illustrate embodiments of the present disclosure and, together with the description, serve to explain the related principles.

BRIEF DESCRIPTION OF THE DRAWINGS

A full and enabling description of the present disclosure, directed to one of ordinary skill in the art, is set forth in the specification, which makes reference to the appended figures, in which.

DETAILED DESCRIPTION

Figure 1:
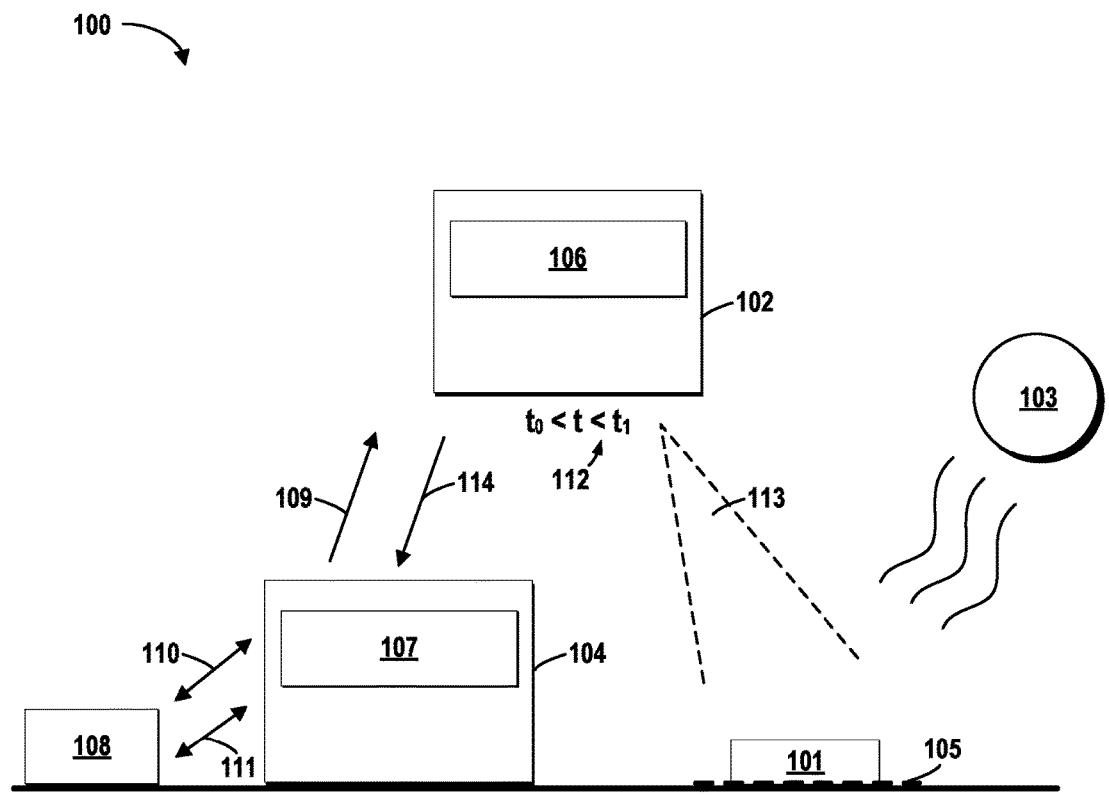
FIG. 1 depicts an example system for enhancing object feature visibility for overhead imaging according to example embodiments of the present disclosure.

Reference now will be made in detail to embodiments of the present disclosure, one or more examples of which are illustrated in the drawings. Each example is provided by way of explanation of the present disclosure, not limitation of the present disclosure. In fact, it will be apparent to those skilled in the art that various modifications and variations can be made to the present disclosure without departing from the scope or spirit of the disclosure. For instance, features illustrated or described as part of one embodiment can be used with another embodiment to yield a still further embodiment. Thus, it is intended that the present disclosure covers such modifications and variations as come within the scope of the appended claims and their equivalents.

Example aspects of the present disclosure are directed to enhancing object feature visibility for overhead imaging. For instance, a ground based computing system (e.g., associated with a control center) can determine one or more image capture condition(s) for an imaging platform (e.g., included on a satellite). The image capture condition(s) can include one or more constraint(s) for the imaging platform to follow while collecting an image. For example, the image capture condition(s) can specify a range of elevation angles and/or a range of azimuth angles at which the imaging platform should obtain image frames of a target object (e.g., a black automobile). The elevation and azimuth ranges can be associated with the positions of the imaging platform, relative to the sun, at which the target object experiences a specular reflection (e.g., a mirror-like reflection due to the incidence angle of the sun's radiation and/or the position of the imaging platform). The specular reflection can be associated with a higher level of reflectance than associated with the surroundings of the target object. The computing system can send, to the imaging platform, a first set of data indicative of the positional ranges. Using this data, the imaging platform can determine when its elevation angle and azimuth angles are within the positional ranges and obtain a plurality of image frames including the target object, which may experience a specular reflection (while its surroundings may not experience such a specular reflection). The imaging platform can send the image frames to the ground based computing system, which can coordinate the processing of the image frames to create an image of the target object.

By creating an image of the target object with a specular reflection, a user of a computing system and/or an image processing system using machine learning techniques can better distinguish the target object (e.g., a black automobile) from a similar surrounding (e.g., an asphalt parking lot). For instance, the specular reflection (and the specular angles) can create a 20,000% difference (e.g., in reflectance) between the target object and its surroundings. This can be beneficial, for example, to more accurately determine the number of automobiles in a parking lot.

More specifically, a ground-based computing system can be configured to create one or more image capture condition(s) for capturing an image of a target object. The target object can include, for example, an automobile, a pile of coal, and/or other objects with which a specular reflection can be created (e.g., due to a glossy surface). The image capture condition(s) can include one or more factor(s) (e.g., if/then statements) that must be met by the imaging platform while it obtains a plurality of image frames. For instance, the image capture condition(s) can include location information (e.g., geographic coordinates) associated with a region of interest and/or the target object. The imaging platform can use the location information to adjust its sensors in a particular direction such that it can obtain a plurality of image frames of the region of interest. Some of the image frames can include, at least a portion of, the target object. By way of example, the imaging platform can use the location information associated with an asphalt parking lot to adjust its sensors such that it can capture image frames of the parking lot as well as a target automobile within the parking lot.

Additionally, and/or alternatively, the image capture condition(s) can include one or more positional range(s) of the imaging platform relative to a solar source (e.g., the sun, a star, a reflective moon). The computing system can obtain information indicative of one or more location(s) of the imaging platform and information indicative of one or more location(s) of the solar source. Based on this information, the computing system can determine when the target object will experience a specular reflection for the purposes of imaging. For instance, the target object can experience a specular reflection when the imaging platform is at certain elevation angles and certain azimuth angles relative to the solar source, due to the angle of incidence and reflection of the solar source's radiation. In some implementations, the target object may experience a specular reflection when the elevation angle of the imaging platform is within +/−5 degrees of the elevation angle of the solar source and when the azimuth angle of the imaging platform is within +/−165 to 195 degrees of the azimuth angle of the solar source, as further described herein. The computing system can send a first set of data indicative of the one or more image capture condition(s) (including the positional range(s)) to the imaging platform.

The imaging platform can receive the first set of data from the computing system. For instance, the imaging platform can be an overhead imaging platform, such as a satellite, an airplane, a helicopter, an unmanned aerial vehicle (UAV), a drone, a balloon, etc. The imaging platform can travel at a height above a region of interest that contains the target object. By way of example, in the event that the imaging platform is included on a satellite orbiting the earth (e.g., above a parking lot), the imaging platform can receive the first set of data indicative of the one or more image capture condition(s) (including the positional range(s)) from one or more ground station(s) distributed globally.

The imaging platform can determine whether it is within the positional range(s) specified by the image capture condition(s). For instance, in some implementations, the imaging platform can include a navigation system (e.g., a global positioning system) to determine its location. Using the navigation system, the imaging platform can determine whether its elevation angle is within the specified range of elevation angles (e.g., +/−5 degrees relative to the elevation angle of the solar source) and/or whether its azimuth angle is within the specified range of azimuth angles (e.g., +/−165 to 195 degrees relative to the azimuth angle of the solar source). If so, the imaging platform can be located at a position at which the target object (e.g., a black automobile) may experience a specular reflection, while its surroundings may not experience such a specular reflection, due to the solar source's radiation interacting with the target object (e.g., its shiny, reflective surface).

In some implementations, the imaging platform can determine its position based on time. For instance, the computing system can determine (e.g., based on Two Line Elements, publically available data) a time range in which the imaging platform will be within the positional range(s). The image capture condition(s), sent to the imaging platform, can include this time range. Using a clock device, the imaging platform can determine when it is within the specified elevation angle and azimuth angle ranges based, at least in part, on a comparison of a current time to the time range.

The imaging platform can obtain a set of data indicative of a plurality of image frames when the position of the imaging platform is within the specified positional range(s) (e.g., when the target object experiences a specular reflection). One or more of the image frame(s) can depict, at least a portion of, the target object. For example, when the imaging platform is at an elevation angle that is within +/−5 degrees of the elevation angle of the solar source and the imaging platform is at an azimuth angle that is within +/−165 to 195 degrees of the azimuth angle of the solar source, the imaging platform can obtain the image frame(s) depicting, at least a portion of, a black automobile.

The imaging platform can send the data indicative of the image frame(s) to the computing system. The computing system can be configured to receive the image frame(s) and coordinate the processing of the image data. For example, the computing system can send the data indicative of the image frame(s) that depict, at least a portion of, a black automobile for processing by another computing system. Processing techniques can include mosaicing the image frame(s) together to reconstruct an image of an asphalt parking lot that includes the black automobile. The automobile can then be distinguished from its surroundings by an image processing computing system (e.g., via machine learning techniques) or a user of a computing system (e.g., via crowdsourcing techniques) based, at least in part, on the specular reflection of the automobile relative to its surroundings.

In accordance with the above, and as will be further described below, the apparatuses, systems, and methods of the present disclosure provide enhanced feature visibility for a target object of an overhead imaging system. More specifically, the systems and methods of the present disclosure can improve optical difference by obtaining images of target objects while they experience a specular reflection. Accordingly, the target objects can be more efficiently and reliably distinguished from their surroundings during post-reconstruction processing. In this way, the systems and methods of the present disclosure can help facilitate the identification of target objects in images, such as low dynamic range images by widening the limited range. Moreover, this can provide a fundamental improvement in the signal quality of images being analyzed, while reducing the need for expensive, higher resolution imaging platforms.

With reference now to the figures, example aspects of the present disclosure will be discussed in greater detail. FIG. 1 depicts an example system 100 for enhancing object feature visibility for overhead imaging according to example embodiments of the present disclosure. As shown, system 100 can include a target object 101, an imaging platform 102, a solar source 103, and a computing system 104. Imaging platform 102 and computing system 104 can be configured to communicate with one another. For example, imaging platform 102 and computing system 104 can be configured to communicate using radio frequency transmission signals.

Target object 101 can be included within a region of interest 105. Region of interest 105 can be an area within the earth's atmosphere, such as on the earth's surface. Region of interest 105 can be, for instance, a parking lot, a port, a quarry, and/or other areas on the earth's surface. Target object 101 can be an object for which imaging platform 102 can be configured to target for one or more image frame(s). Target object 101 can include, for instance, at least one of an automobile, a pile of coal, and/or other object's located in region of interest 105. Target object 101 can include a glossy reflective surface. One or more image(s) of target object 101 can be used to estimate a state associated with region of interest 105 and/or target object 101. For example, the image(s) of target object 101 can be used to determine the number of automobiles in a parking lot, the depth of a coal pile, etc.

Imaging platform 102 can be configured to travel overhead region of interest 105 to acquire images. For instance, imaging platform 102 can be associated with a satellite, an aircraft, a helicopter, an unmanned aerial vehicle (UAV), a drone, a balloon, etc. Imaging platform 102 can include one or more computing device(s) 106. Computing device(s) 106 can include one or more processor(s) and one or more memory device(s). The memory device(s) can be configured to store instructions that when executed by the processor(s), cause imaging platform 102 to perform operations, such as those for enhancing the visibility of target object 101 for overhead imaging, as further described herein.

Imaging platform 102 can be configured to travel in a path over region of interest 105 called a track. The path can include one or more straight lines or segments or can be a curved path. In the event that imaging platform 102 is associated with a satellite, the path can correspond to, at least a portion of, the orbit of the satellite. Imaging platform 102 can be flown at a height over region of interest 105. As further described herein with reference to FIGS. 4-7, imaging platform 102 can be configured to obtain a plurality of image samples or frames during the travel of the platform along the path. In some implementations, the image frames can be captured in a continuous, rapid succession. The image frames can then be assembled into an output image on the ground via digital processing, as further described herein.

Solar source 103 can be associated with a light source that can project light onto and/or in the vicinity of target object 101 and/or region of interest 105. In some implementations, solar source 103 can be a natural source (e.g., celestial body) that projects electromagnetic radiation (e.g., light) onto target object 101 and/or region of interest 105. For instance, solar source 103 can include the sun, a star, a reflective moon, etc. In some implementations, solar source 103 can include a man-made light source that is situated above target object 101 and/or region of interest 105 and oriented to project light onto target object 101 and/or region of interest 105.

Computing system 104 can be associated with a ground-based computing system. For instance, computing system 104 can be associated with a control center that is responsible for monitoring and controlling imaging platform 102 (e.g., via command signals). Computing system 104 can include one or more computing device(s) 107. Computing device(s) 107 can include one or more processor(s) and one or more memory device(s). The memory device(s) can be configured to store instructions that when executed by the processor(s), cause computing device(s) 107 to perform operations, such as those for enhancing the visibility of target object 101 for overhead imaging, as further described herein (e.g., method 800).

Computing device(s) 107 can be configured to obtain information about the locations of imaging platform 102 and/or solar source 103. For instance, computing device(s) 107 can be configured to obtain a first set of information 110 associated with one or more location(s) of imaging platform 102 and/or a second set of information 111 associated with one or more location(s) of solar source 103. In some implementations, the first and second sets of information 110, 111 can include data associated with global position systems, speed, orbit, etc. Computing device(s) 107 can be configured to obtain the first and/or second sets of information 110, 111 from one or more remote database(s) 108. In some implementations, remote database(s) 108 can be privately available, publically available (e.g., a database associated with a satellite tracking website), and/or associated with a governmental agency (e.g., National Oceanic and Atmospheric Administration, National Aeronautics and Space Administration).

Computing device(s) 107 can be configured to determine the travel paths of imaging platform 102 and/or solar source 103. For instance, computing device(s) 107 can be configured to use a two-line element set (TLE) (e.g., associated with the first and second sets of information 110, 111) to determine past and future points on the travel paths (e.g., orbital paths) of imaging platform 102 and/or solar source 103. In some implementations, computing device(s) 107 can update the travel paths of imaging platform 102 and/or solar source 103 stored in its memory device(s) to match the TLEs periodically (e.g., once, twice, three times per day). In this way, computing device(s) 107 can accurately determine the locations of imaging platform 102 and/or solar source 103 (e.g., latitude, longitude, elevation, elevation angle, azimuth angle) throughout a day.

Computing device(s) 107 can be configured to determine one or more image capture condition(s) for capturing an image of target object 101. Image capture condition(s) can include one or more factor(s) for imaging platform 102 to follow while imaging platform 102 obtains a plurality of image frames. For instance, the image capture condition(s) can include location information (e.g., coordinates) associated with region of interest 105 and/or target object 101. Imaging platform 102 can use the location information to adjust its sensors such that it can obtain a plurality of image frames of region of interest 105, some of which can include, at least a portion of, target object 101. By way of example, imaging platform 102 can use the location information associated with an asphalt parking lot to adjust its sensors such that it can capture image frames of the parking lot, as well as, image frames that include, at least a portion of, a target automobile within the parking lot.

Additionally, and/or alternatively, image capture condition(s) can include one or more positional range(s) of imaging platform 102 relative to solar source 103. Computing device(s) 107 can be configured to determine one or more positional range(s) of imaging platform 102 relative to solar source 103 based, at least in part, on the first and second sets of information 110, 111. The one or more positional range(s) can be indicative of one or more position(s) at which imaging platform 102 is to obtain one or more image frame(s) depicting at least a portion of target object 101.

In some implementations, the positional range(s) can be associated with one or more position(s) of solar source 103 at which radiation (e.g., light) from solar source 103 causes a specular reflection with target object 101, while a surrounding of target object 101 may not experience such a level of specular reflection. For instance, target object 101 can experience a specular reflection when imaging platform 102 is at certain elevation angles and/or certain azimuth angles relative to solar source 103, due to the angle of incidence and angle of reflection of the radiation of solar source 103. In this way, computing device(s) 107 can restrict image angles depending on the location of solar source 103, to include glint or glare associated with target objects 101.

Figure 2:
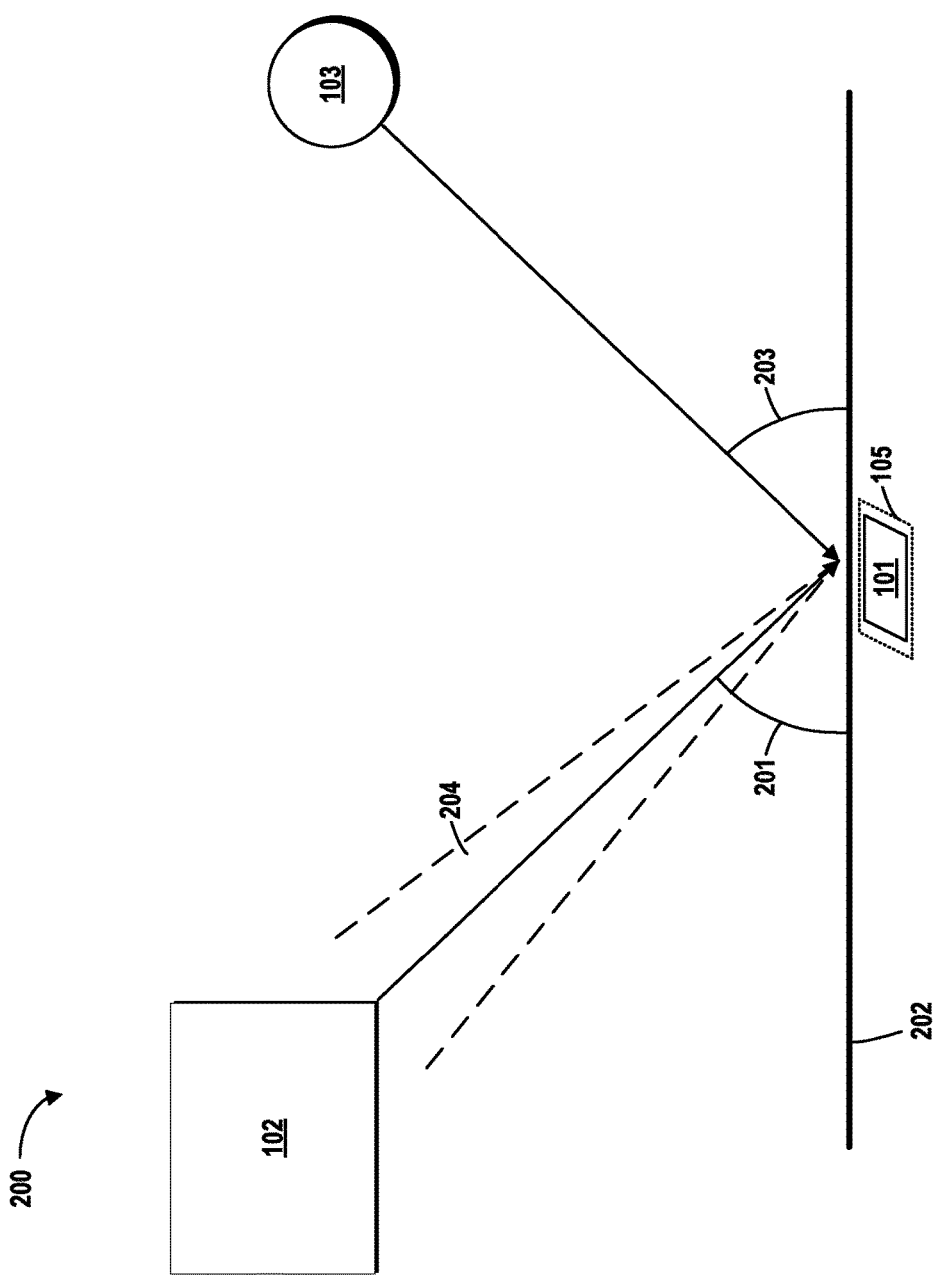
FIG. 2 illustrates an example schematic of an imaging platform elevation angle relative to a target and a solar source according to example embodiments of the present disclosure.

FIG. 2 illustrates an example schematic 200 of the elevation angle of imaging platform 102 relative to target object 101 and solar source 103 according to example embodiments of the present disclosure. As shown, imaging platform 102 and solar source 103 can be oriented above region of interest 105 and/or target object 101. Imaging platform 102 can be located at an elevation angle 201 relative to a horizontal plane 202 associated with region of interest 105 and/or target object 101. Solar source 103 can be located at an elevation angle 203 relative to horizontal plane 202 associated with region of interest 105 and/or target object 101.

Target object 101 can experience a specular reflection (while its surroundings may not) when imaging platform 102 is within a first positional range 204. First range 204 can include one or more elevation angle(s) 201 of imaging platform 102 that are within a certain degree of the elevation angle 203 of solar source 103. The elevation angle(s) 201 included in first range 204 can be associated with the angles of incidence and/or reflection of the radiation of solar source 103 that cause specular reflection with target object 101. For instance, target object 101 can experience a specular reflection when elevation angle 201 of imaging platform 102 is substantially the same as elevation angle 203 of solar source 103. In some implementations, first range 204 can include one or more elevation angle(s) of imaging platform 102 that are within +/−5 degrees of elevation angle 203 of solar source 103. By way of example, in the event that elevation angle 203 of solar source 103 is 45 degrees relative to horizontal plane 202, the first range 204 can include the elevation angles 201 of imaging platform 102 from 40 to 50 degrees relative to horizontal plane 202.

Figure 3:
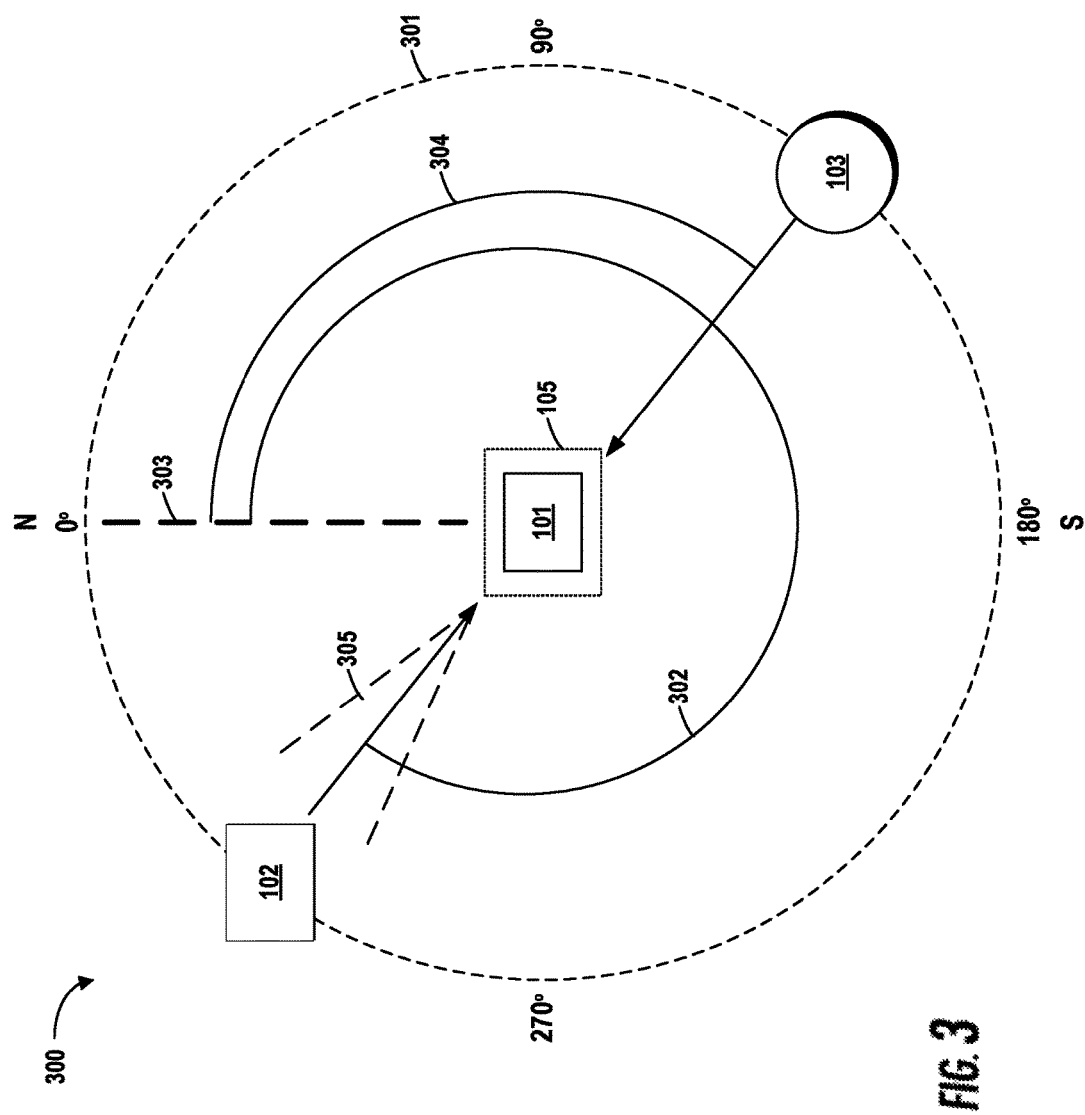
FIG. 3 illustrates an example schematic of an imaging platform azimuth angle relative to a target and a solar source according to example embodiments of the present disclosure.

FIG. 3 illustrates an example schematic 300 of the azimuth angle of imaging platform 102 relative to target object 101 and solar source 103 according to example embodiments of the present disclosure. As shown, imaging platform 102 and solar source 103 can be oriented within a reference plane 301 that includes region of interest 105 and/or target object 101. Imaging platform 102 can be located at an azimuth angle 302 relative to a reference vector 303 (e.g., within reference plane 301) associated with region of interest 105 and/or target object 101. Solar source 103 can be located at an azimuth angle 304 relative to reference vector 303 associated with region of interest 105 and/or target object 101.

Target object 101 can experience a specular reflection when imaging platform 102 is within a second positional range 305. Second range 305 can include one or more azimuth angle(s) 302 of imaging platform 102 that are within a certain degree of azimuth angle 304 of solar source 103. The azimuth angle(s) 302 included in second range 305 can be associated with the angles of incidence and/or reflection of the radiation of solar source 103 that cause a specular reflection with target object 101 rather than at least one other portion of region of interest 105 (e.g., due to the lack of glossy, reflective surface of that portion). In some implementations, second range 305 can include one or more azimuth angle(s) 302 of imaging platform 102 that are within +/−165 degrees to 195 degrees of azimuth angle 304 of solar source 103. Said differently, the azimuth angle 302 of imaging platform 102 can be within +/−15 degrees of 180 degrees of azimuth angle 304 of solar source 103. By way of example, in the event that azimuth angle 304 of solar source 103 is 135 degrees relative to reference vector 303 (e.g., associated with compass North), second range 305 can include the azimuth angles 302 of imaging platform 102 from 300 to 330 degrees relative to reference vector 303.

Returning to FIG. 1, computing device(s) 107 can be configured to determine the first and second ranges 204, 305 based, at least in part, on the first and second sets of information 110, 111 associated with the location(s) of imaging platform 102 and solar source 103. The one or more positional range(s) (indicated by the image capture condition(s)) can include first range 204 associated with elevation angle 201 of imaging platform 102 and/or second range 305 associated with azimuth angle 302 of imaging platform 102.

Computing device(s) 107 can be configured to determine when imaging platform 102 will enter the first and second ranges 204, 305. For instance, computing device(s) 107 can determine a time range 112 in which imaging platform 102 is within the one or more positional range(s) (e.g., 204, 305) of imaging platform 102 relative to solar source 103. Computing device(s) 107 can determine time range 112 based, at least in part, on first set of information 110, second set of information 111, first range 204, and/or second range 305. Time range 112 can include a first time ($t_0$) that is indicative of when the position of imaging platform 102 will enter first range 204 associated with elevation angle 201 of imaging platform 102 and second range 305 associated with azimuth angle 302 of imaging platform 102. Time range 112 can also include a second time ($t_1$) that is indicative of when the position of imaging platform 102 will exit at least one of first range 204 associated with elevation angle 201 of imaging platform 102 or second range 305 associated with azimuth angle 302 of imaging platform 102. Based, at least in part, on time range 112, computing device(s) 107 can be configured to determine the imaging access for target object 101 and select precise collection times within that access, to optimize for imaging platform 102 and solar source 103 geometry. This can lead to the highest level of reflectance with target object 101 during image collection.

By way of example, target object 101 (e.g., a black automobile) can be located within region of interest 105 (e.g., an asphalt parking lot) during the hours of 8:00 a.m. PST to 11:00 a.m. PST. At 9:30 a.m. PST, elevation angle 203 of solar source 103 can be 45 degrees and azimuth angle 304 of solar source 103 can be 135 degrees. Computing device(s) 107 can be configured to determine that at 9:20 a.m. PST (e.g., first time $t_0$) elevation angle 201 of imaging device 102 can be 40 degrees and azimuth angle 302 of imaging platform 102 can be 300 degrees. Computing device(s) 107 can be configured to determine that at 9:40 a.m. PST (e.g., second time $t_1$) elevation angle 201 of imaging device 102 can be 50 degrees and azimuth angle 302 of imaging platform 102 can be 330 degrees. Thus, time range 112 can include times from 9:20 a.m. PST (e.g., first time $t_0$) to 9:40 a.m. PST (e.g., second time $t_1$) during which target object 101 may experience a specular reflection and which imaging platform 102 can be directed to capture image frames of target object 101 and/or region of interest 105.

Computing device(s) 107 can be configured to send a first set of data 109 indicative of one or more image capture condition(s) to imaging platform 102, which can be configured to receive the first set of data 109. Such data can be sent, for example, via one or more radio frequency transmission signal(s). The image capture condition(s) can be indicative of the one or more positional range(s) (e.g., 204, 305) of imaging platform 102 relative to solar source 103. For example, the positional range(s) (e.g., 204, 305) of imaging platform 102 relative to solar source 103 can include first range 204 associated with elevation angle 201 of imaging platform 102 (e.g., +/−5 degrees of elevation angle 203 of solar source 103) and second range 305 associated with azimuth angle 302 of imaging platform 102 (e.g., within 165 degrees to 195 degrees of azimuth angle 304 of solar source 103).

Imaging platform 102 can be configured to determine whether the image capture condition(s) exist such that it can begin to collect image frames. For instance, imaging platform 102 can be configured to determine whether a position of imaging platform 102 is within the one or more positional range(s) (e.g., 204, 305), indicated by the image capture condition(s). In some implementations, imaging platform 102 can include a navigation system (e.g., a global positioning system) to determine its location. Using the navigation system, imaging platform 102 can determine whether its elevation angle 201 is within first range 204 (e.g., +/−5 degrees relative to elevation angle 203 of solar source 103) and/or whether its azimuth angle 302 is within second range 305 (e.g., +/−165 to 195 degrees relative to azimuth angle 304 of solar source 103). If so, imaging platform 102 can be located at a position at which target object 101 (e.g., a black automobile) can experience a specular reflection due to the radiation from solar source 103.

In some implementations, imaging platform 102 can determine its position based on time. For instance, the first set of data 109 receive by imaging device 102 can be indicative of time range 112, identifying when imaging platform 102 is within the one or more positional range(s) (e.g., 204, 305). Using a clock device, computing device(s) 106 of imaging platform 102 can determine when imaging platform 102 is within first range 204 (e.g., elevation angle range) and/or second range 305 (e.g., azimuth angle range) based, at least in part, on whether a time associated with imaging platform 102 (e.g., a current time) is within time range 112.

In some implementations, computing device(s) 107 can be configured to determine whether the image capture condition(s) exist. For instance, computing device(s) 107 can be configured to determine whether imaging platform is oriented to capture image frame(s) including, at least a portion of, region of interest 105 and/or target object 101. Computing device(s) 107 can determine whether a position of imaging platform 102 is within the one or more positional range(s) (e.g., 204, 305). Computing device(s) 107 can determine whether a time associated with imaging platform 102 is within time range 112. Computing device(s) 107 can make such determinations, based, at least in part, on the first and second sets of information 110, 111 and/or on one or more communications (e.g., radio frequency transmission signals) sent to and/or received from imaging platform 102.

Computing device(s) 106 of imaging platform 102 can be configured to obtain a plurality of image frames. For instance, using the systems and methods described with reference to FIGS. 4-7, computing device(s) 106 can be configured to obtain a second set of data 113 that is indicative of a plurality of image frames based, at least in part, on the one or more positional range(s) (e.g., 204, 305). Each image frame can depict, at least a portion of, region of interest 105. Moreover, one or more of the image frame(s) can depict, at least a portion of, target object 101 in region of interest 105.

For instance, target object 101 can be a black automobile that is located within region of interest 105, for example, a black asphalt parking lot. When imaging platform 102 is within the positional range(s) (e.g., 204, 305) relative to solar source 103 and/or time range 112, imaging platform 102 can be configured to obtain a second set of data 113 indicative of one or more image frame(s). One or more of the image frame(s) can include, at least a portion of, target object 101 (e.g., the black automobile). In this way, the image frame(s) will be obtained when target object 101 experiences a specular reflection due to the orientation of solar source 103 (and/or imaging platform 102). Moreover, the portion of target object 101 depicted in one or more of the image frame(s) may be associated with a specular reflection, while the other portions of region of interest 105 depicted in the image frame(s) may not experience such a level of reflectance. Imaging platform 102 can be configured to send, to computing device(s) 107 (e.g., that are remote from imaging platform 102), a third set of data 114 that is indicative of at least the one or more image frame(s) that depict, at least a portion of, target object 101.

In some implementations, computing device(s) 107 can be configured to command imaging platform 102 to capture one or more image frame(s). For instance, when computing device(s) 107 determine that imaging platform 102 is within first and second ranges 204, 305 (e.g., such that the black automobile is experiencing a specular reflectance due to solar source 103), computing device(s) 107 can be configured to send one or more command signal(s) to imaging platform 102 directing it to obtain second set of data 113 indicative of a plurality of image frames. Imaging platform 102 can be configured to receive the one or more command signal(s) and can obtain second set of data 113 indicative of a plurality of image frames. Each image frame can include, at least a portion of, region of interest 105. One or more of the image frame(s) can depict, at least a portion of, target object 101. The portion of target object 101 depicted in one or more of the image frame(s) may be associated with the specular reflectance, while one or more other portion(s) of region of interest 105 may not.

Computing device(s) 107 can be configured to receive the third set of data 114 and coordinate processing of the image frame(s). For example, computing device(s) 107 can be configured to send the third set of data 114 that is indicative of the one or more image frame(s) depicting (at least a portion of) target object 101 to another computing system for processing. For instance, processing techniques can include mosaicing the image frames together to reconstruct an image of an asphalt parking lot, including the black automobile, as further described herein.

Target object 101 can then be distinguished from its surroundings. For example, a threshold can be indicative of a level of brightness and/or reflectance expected to be associated with target object 101 when it experiences a specular reflection. An image processing computing system employing machine learning techniques and/or a user of the image processing computing system can examine the images of target object 101, looking for portions with a level of brightness and/or reflectance that is above the threshold. By way of example, an image processing computing system can examine an image of the black automobile in the black asphalt parking lot. The image processing computing system can look for the glint or glare produced from the black automobile as it experiences a specular reflection (while its surroundings may not) based, at least in part, on the orientation of imaging platform 102 in the positional range(s) (e.g., 204, 305). If the portion of the image has a level of brightness and/or reflectance that is above the threshold, the image processing computing system (and/or its user) can distinguish a black automobile from the black asphalt parking lot in which it is located. This can help, for instance, to estimate a number of automobiles that are currently parked in a parking lot.

FIGS. 4-7 depict example embodiments of imaging platform 102, example embodiments of its components, and example embodiments of imaging capture and processing techniques. The embodiments shown and described with reference to FIGS. 4-7 are intended as examples and are not intended to be limiting. Imaging platform 102 can include different types, numbers, orientations, combinations, etc. of components than those shown and described herein. Moreover, different imaging capture and processing techniques can be implemented in the systems, methods, and apparatuses of the present disclosure than those described herein. The systems, methods, and apparatuses of the present disclosure can be implemented in any imaging system.

Figure 4:
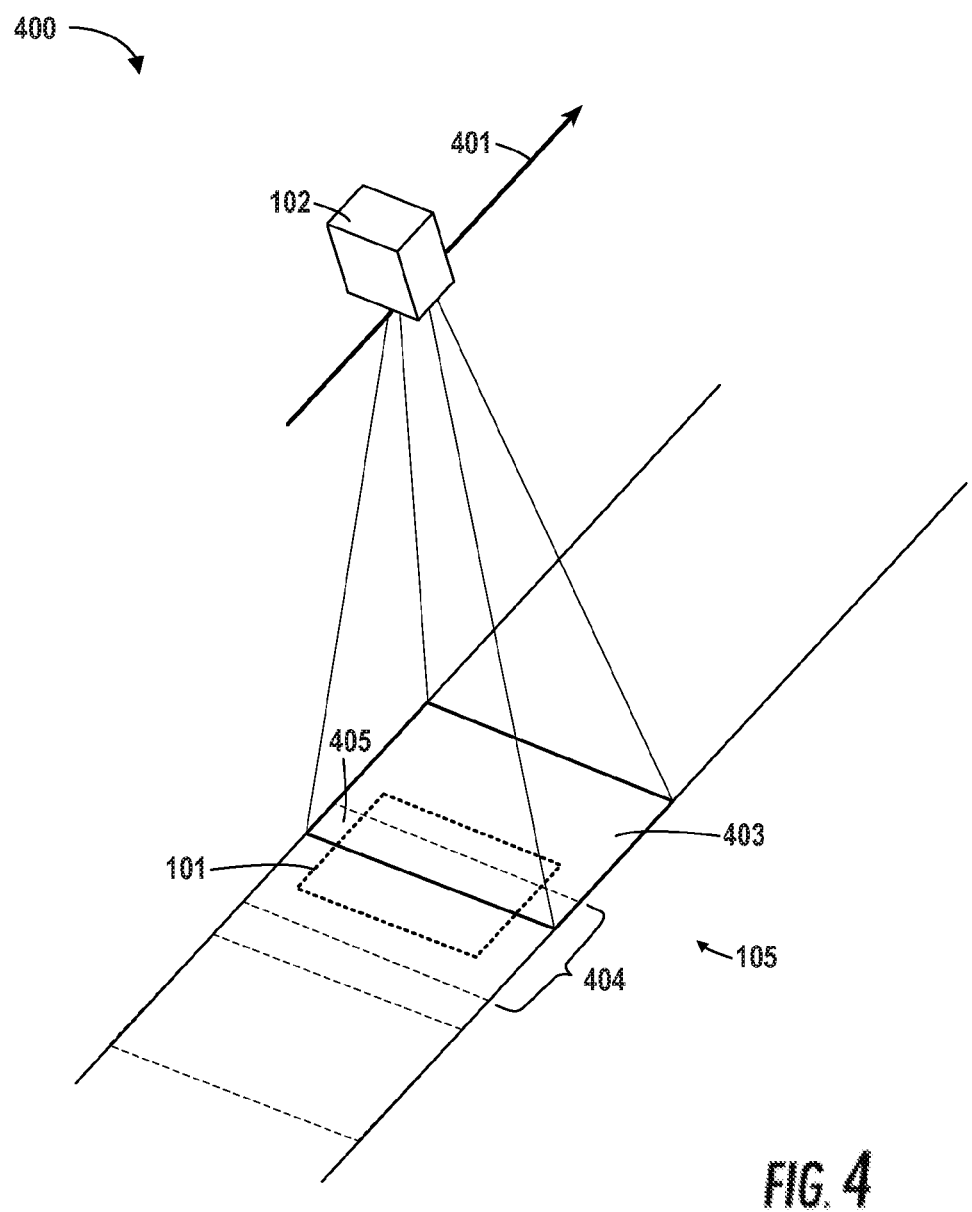
FIG. 4 depicts an example imaging platform according to example embodiments of the present disclosure.

FIG. 4 depicts an example imaging platform 102 according to example embodiments of the present disclosure. Imaging platform 102 can be configured to use one or more 2D staring sensors to acquire entire 2D frames taken as snapshots while imaging platform 102 travels along a track 401 over region of interest 105. In some implementations, imaging platform 102 can be configured such that neighboring images contain overlapping measurements of region of interest 105. For instance, the presence of overlapping regions in the output images allows for later image processing to register neighboring image frames and mosaic the images together to reconstruct an image of region of interest 105 and/or target object 101.

In particular, imaging platform 102 can acquire an entire two-dimensional image frame 403 in a single snapshot. Staring sensors can be configured to capture images in rapid succession. For instance, an image can be captured sequentially through the capture or acquisition of many different image frames (e.g. image frames 403, 404), each of which can have some amount of overlap 405 with the image frames before and/or after it. One or more of the image frame(s) can include, at least a portion of, target object 101. In some implementations, the imaging region of a staring sensor can be thought of as a two-dimensional surface area. Light can be collected and bundled into individual pixels, whereby the number of pixels relative to the surface area of the image region determines the resolution of the staring sensor. In various implementations, the staring sensor can comprise a complementary metal-oxide-semiconductor (CMOS) sensor or a charge coupled device (CCD) sensor. The staring sensor can include an array of photodiodes. In some implementations, the staring sensor includes an active-pixel sensor (APS) comprising an integrated circuit containing an array of pixel sensors. Each pixel sensor can include a photodiode and an active amplifier. For some overhead imaging implementations, the staring sensor (and/or other components of an overhead imaging platform) can be radiation hardened to make it more resistant to damage from ionizing radiation in space.

As indicated, imaging platform 102 can be configured such that neighboring image frames 403, 404 contain overlapping measurements of region of interest 105 (e.g., the overlap 405). The presence of overlapping regions in the output images allows for later image processing to register neighboring image frames and to combine the images together to reconstruct a more accurate image of region of interest 105. In addition, by combining many separate similar image frames together, the final reconstructed image captured by a staring sensor can correct for deviations in the motion of imaging platform 102 from the expected direction of travel 401, including deviations in speed and/or direction.

In some implementations, imaging platform 102 can further include a color wheel sensor, a color filter array (CFA), such as a Bayer filter, a panchromatic channel (e.g. panchromatic filter or panchromatic sensor), one or more spectral channels (e.g. spectral sensor or spectral filter), etc. For instance, imaging platform 102 can include an imaging sensor having a panchromatic block adjacent to a multispectral block. In some implementations, imaging platform 102 can include a one-dimensional line sensor, such as a TDI sensor. A line scan sensor can be a sensor having a single row of pixels for each color to be collected. The sensor is positioned in imaging platform 102 so as to be perpendicular to the track direction thus moving in a linear manner across a scene. Each row of pixels in an image is exposed in sequence as the sensor moves across the scene, thus creating a complete 2D image. When imaging platform 102 captures images with multispectral (e.g., multiple color) information, it can use an independent line scan sensor for each spectrum (e.g., color band) to be captured, wherein each line scan sensor is fitted with a different spectral filter (e.g., color filter).

Figure 5:
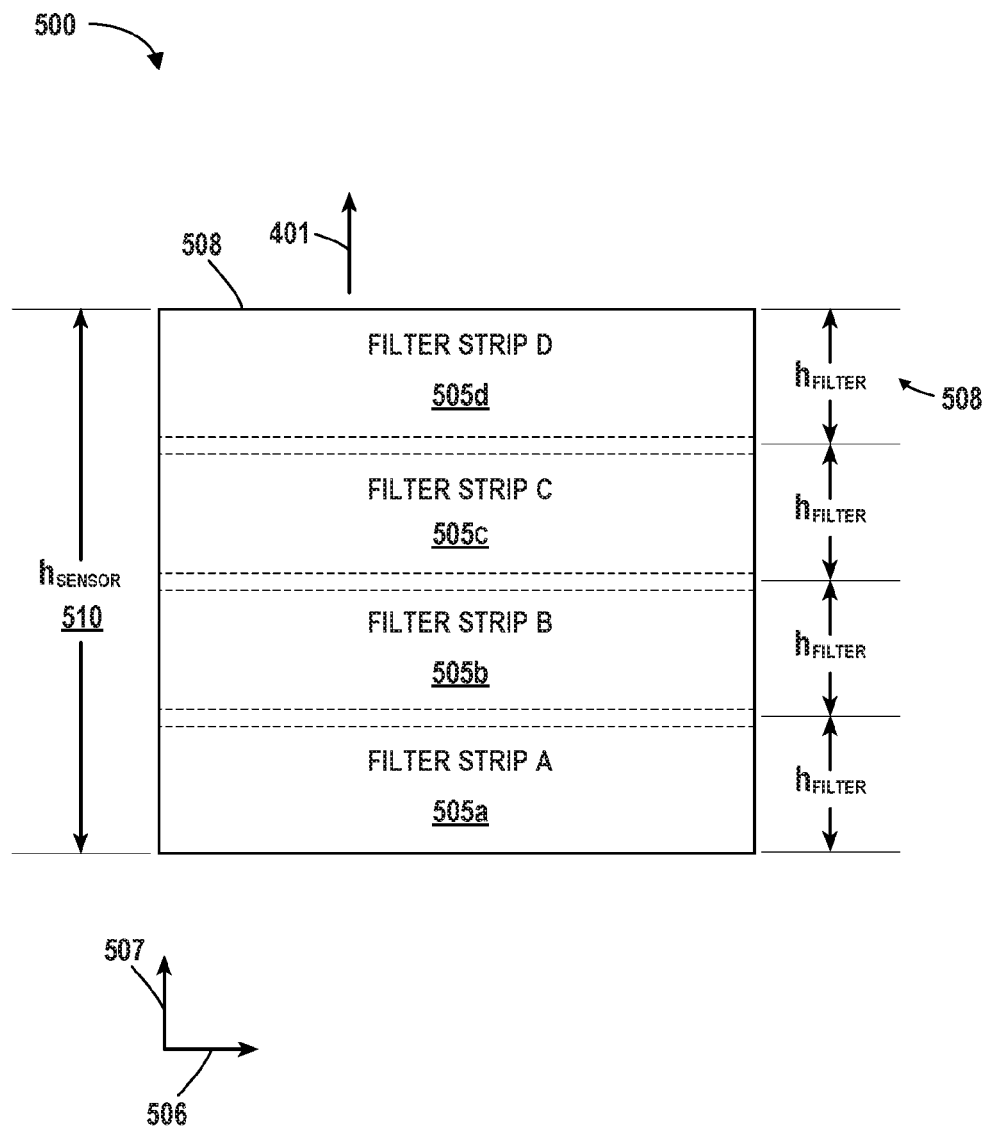
FIGS. 5-6 depict example imaging sensor configurations according to example embodiments of the present disclosure.

FIG. 5 depicts an example filter configuration for a two-dimensional multispectral staring sensor 500 that includes spectral filter strips 505a, 505b, 505c, and 505d, according to example embodiments of the present disclosure. In particular, staring sensor 500 can include a block 508 of a plurality of spectral filter strips 505a-505d. In this example, spectral filter strips 505a-505d can be shaped in a long, narrow manner spanning the axis or surface area of the staring sensor 500. Spectral filter strips 505 can be disposed relative to the surface of staring sensor 500 such that filter strips 505a-505d are disposed between the surface of staring sensor 500 and region of interest 105 to be captured in an image. As indicated above, region of interest 105 can include, for example, a portion of the surface of the earth that is to be imaged from imaging platform 102. Region of interest 105 can include target object 101. Light from region of interest 105 and/or target object 101 can pass through filter strips 505a-505d before being detected by photosensitive elements of staring sensor 500. Filter strips 505a-505d can be formed over or on staring sensor 500 or can be attached or bonded to staring sensor 500. For example, filter strips 505a-505d can be bonded to a ceramic carrier or substrate for staring sensor 500.

The structure of staring sensor 500 can be described with reference to two perpendicular axes 506, 507, with the axis 507 in the expected direction of travel 401 of imaging platform 102. For instance, filter strips 505a-505d can be oriented perpendicular to axis 507 in the direction of travel 401. Each filter strip 505a-505d can have a longitudinal axis that is oriented perpendicular to the axis 507 in the direction of travel 401 of imaging platform 102. Each filter strip 505a-505d can have a height in the direction 507. In some implementations, the width of filter strips 505a-505d along the direction 506 (perpendicular to the direction of motion 401) can be substantially the same as the length of staring sensor 500 in that direction, such that filter strips 505a-505d substantially cover the surface of staring sensor 500.

In one example implementation, staring sensor 500 can include at least four spectral filter strips (e.g., red, green blue, infrared). Various other suitable numbers of filter strips can be used. Filter strips 505a-505d can be shaped roughly as rectangles (e.g., as shown in FIG. 5) or as parallelograms, squares, polygons, or any other suitable shape. In various implementations, filter strips 505a-505d cover substantially the entire surface of staring sensor 500.

Each filter strip 505a-505d can be configured to transmit light within a range of wavelengths. For example, a blue spectral filter strip can be configured to transmit wavelengths of light centered around the color blue (e.g., 450-475 nm). Wavelengths of light outside the range transmitted by a filter are blocked, so that light outside the transmitted range is not collected by the pixels of staring sensor 500 that are "below" the filter strip. The range of wavelengths transmitted by each filter strip 505a-505d can vary. The range of wavelengths transmitted by a particular filter strip 505a-505d may or may not overlap, at least partially, with the range of wavelengths transmitted by other filter strips, depending upon the implementation. In addition to red (R), green (G), blue (B), and infrared (IR) filters as illustrated, there are many other possible wavelength ranges that can be transmitted by a spectral filter, for example cyan, yellow, magenta, or orange. Infrared filters can include near, mid, or far infrared filters. In some implementations, ultraviolet filters can be used. In some implementations, the wavelength ranges (or bandwidths) for filter strips 505a-505d are selected to cover at least a portion of a desired spectral range, e.g., a visible spectral range, an infrared spectral range, an ultraviolet spectral range, or a combination of such spectral ranges. Additionally, the ordering of spectral filters (as well as placement in relation to a panchromatic sensor, if used) along the direction of relative motion 401 can be arbitrary, and as a consequence any order of filter strips 505a-505d can be used.

In some implementations, the height 508 of filter strips 505a-505d along their short edges $h_{filter}$ is between one and four times a minimum filter height. In one implementation, the minimum filter height can correspond to the velocity of a point on the ground as seen by staring sensor 500 as it moves in the direction of travel 401, divided by a frame rate at which staring sensor 500 (and/or the imaging electronics such as associated with computing device(s) 106) captures image frames. In some implementations, computing device(s) 106 can be integrated with sensor 500, which can simplify packaging and use with an imaging system. Computing device(s) 106 can be used or integrated with any of the embodiments of sensor 500 described herein to electronically control image or video capture by sensor 500.

Although FIG. 5 illustrates staring sensor 500 having filter strips 505a-505d that each have the same height 508, this is for purposes of illustration and is not intended to be limiting. In other implementations, the heights of some or all of the filter strips can be different from each other.

In addition to a two dimensional staring sensor, staring sensor 500 optionally can also include a panchromatic block for capturing panchromatic image data in addition to the multispectral image data captured via filter strips 505a-505d of staring sensor 500. The panchromatic block can be sensitive to a wide bandwidth of light as compared to the bandwidth of light transmitted by one or more of filter strips 505a-505d. For example, the panchromatic block can have a bandwidth that substantially covers, at least, a substantial portion of the combined bandwidths of filter strips 505a-505d. In various implementations, the bandwidth of the panchromatic block can be greater than about two, greater than about three, greater than about four, or greater than about five times the bandwidth of a filter strip 505a-505d.

Figure 6:
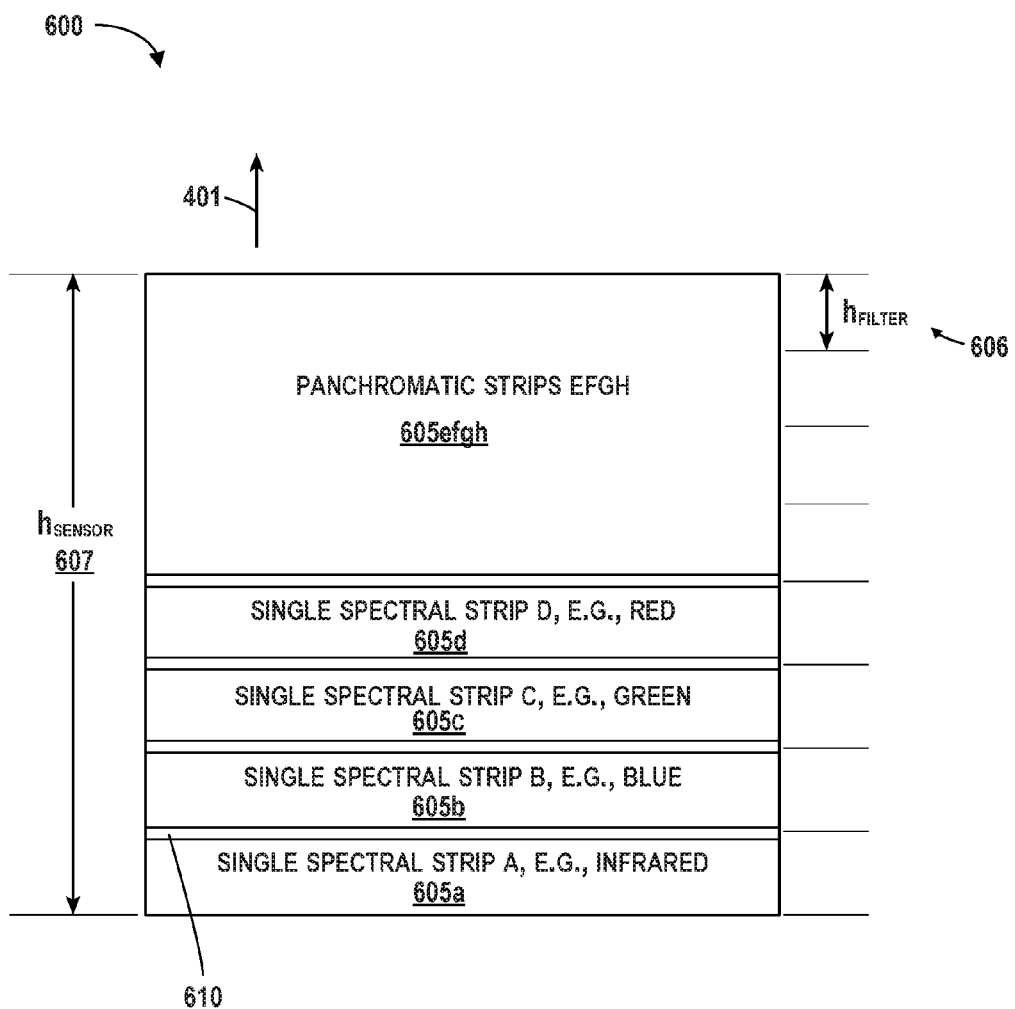

FIG. 6 depicts an example sensor including a two dimensional staring sensor 600 with spectral filter strips 605a-605d and a panchromatic block 605efgh, according to example embodiments of the present disclosure. As shown, panchromatic block 605efgh is the same width (e.g., perpendicular to direction of relative motion 401) as each individual spectral filter strip (e.g., infrared 605a, blue 605b, green 605c, red 605d), but is four times the height 600 (e.g., parallel to the direction of motion 401) of any of the individual spectral filter strips 605a-605d. The height of panchromatic block 605efgh relative to the height of filter strips 605a-605d can vary in various implementations. For instance, the width and height of panchromatic block 605efgh can be determined based on the direction of relative motion 401 of imaging platform 102, where height is parallel to the direction of relative motion 401, and width is perpendicular to the direction of relative motion 401.

FIG. 6 depicts gaps 610 between filter strips 605a-605d and panchromatic strips 605efgh. It will be appreciated that such gaps can be any suitable size. It will further be appreciated that, in some implementations, such gaps may not be included at all. The total height 607 of this implementation of sensor 600 can correspond to the sum of the heights of the panchromatic block 605efgh, filter strips 605a-605d, and gaps 610 (if included).

Although panchromatic block 605efgh includes a single panchromatic filter, it will be appreciated that, in some implementations, panchromatic block 605efgh can include a plurality of panchromatic strips having various suitable proportions. In some implementations, all portions of the spectral sensor(s) and panchromatic sensor(s) imaging areas can have the same pixel size, pixel shape, pixel grid or array placement, and/or pixel density. However, in some cases individual portions of the sensors can have differing pixel sizes, shapes, grid or array placements, and/or densities.

As indicated above, in some implementations, an imaging sensor can include a single (e.g., monolithic) two-dimensional staring sensor, where different portions of the sensor capture different data based on the spectral filters and/or panchromatic filters. In other implementations, multiple staring sensors can be used. For example, the panchromatic strip(s) can be disposed over a first photosensor, and the spectral filter strip(s) can be disposed over a second photosensor. In other implementations, a different photosensor can be used for each spectral or panchromatic strip. The different photosensors can, in some cases, have different pixel arrangements. In other implementations, the staring sensor can be replaced by other types of spectral sensors such as line scanners (including TDI), color wheels, and CFA sensors.

Figure 7:
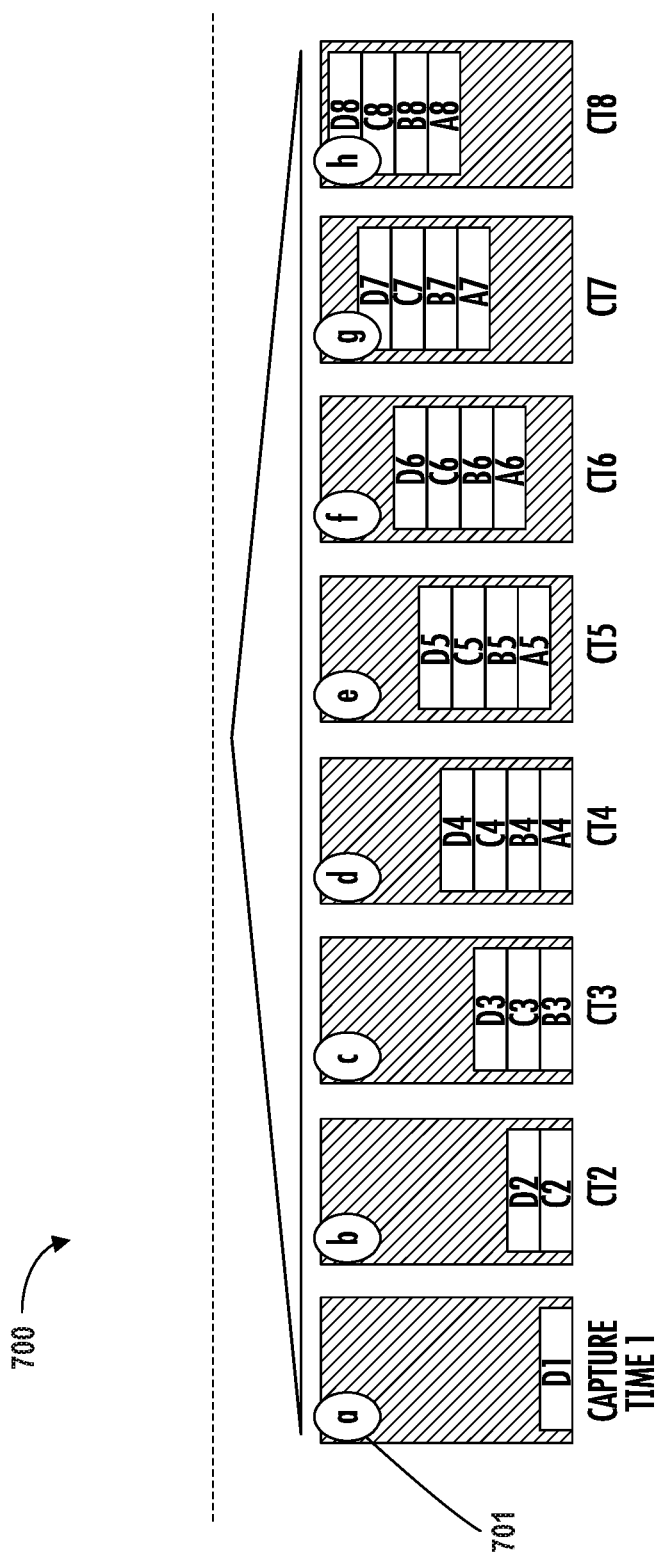
FIG. 7 depicts an example image acquisition sequence according to example embodiments of the present disclosure.

FIG. 7 depicts an example imaging sequence 700 according to example embodiments of the present disclosure. As described herein, imaging platform 102 can move along the track direction, and thus can move relative to region of interest 105 (and/or target object 101) to be observed. Imaging platform 102 can be configured to capture image frames successively at a specified frame rate (frames per second or fps) and/or integration time. As imaging platform 102 moves and captures image frames, one or more point in the region of interest 105 and/or on the target object 101 can be captured at least once by each spectral filter (and/or panchromatic filter).

As depicted in FIG. 7, images 701a-701h represent a sequence of eight successive image frames captured by a sensor scanning over region of interest 105. For instance, image sequence 700 can be captured using a sensor corresponding to staring sensor 500. In this example, a panchromatic channel is not used. As shown, the sensor captures eight image frames, corresponding to capture times (CT) 1-8. The individual sensor captures are denoted by a capital letter for the filter strip (from A to D) followed by a number for the capture time. For example, sensor capture D3 in image CT3 represents the capture by the spectral strip D, 505d, in the third capture time. One or more of the image frame(s) can include at least a portion of target object 101.

In some implementations, after collection, all of the images can be co-registered. Once co-registration is completed, a separate reconstructed spectral image can be created for each color (spectral) band. The reconstructed color band images can be combined to create a multispectral image. In cases where the staring sensor includes a panchromatic sensor in addition to the multispectral sensor, captured panchromatic image data can be used to enhance the quality of a multispectral image.

Figure 8:
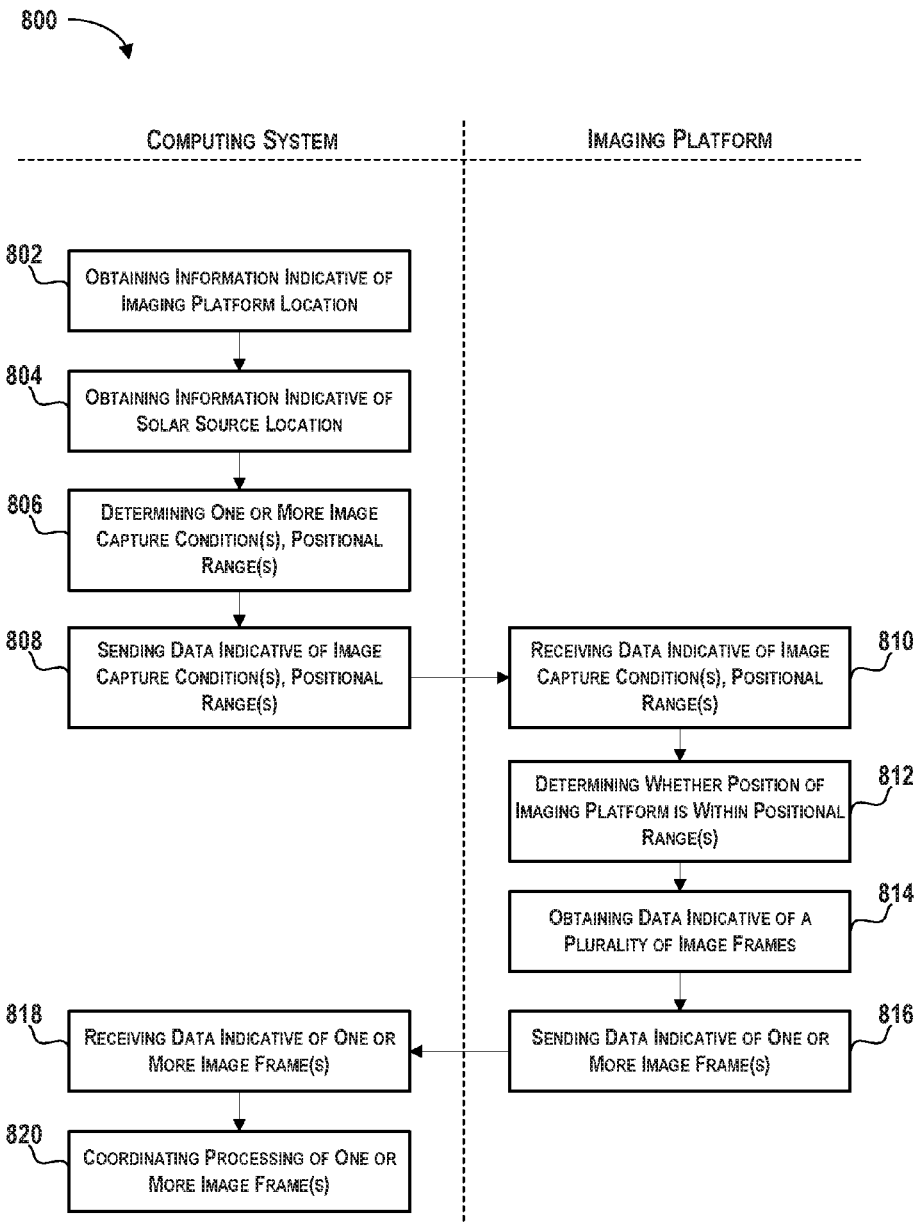
FIG. 8 depicts a flow diagram of an example method of enhancing object feature visibility for overhead imaging according to example embodiments of the present disclosure.

FIG. 8 depicts a flow diagram of an example method 800 of enhancing object feature visibility for overhead imaging according to example embodiments of the present disclosure. Method 800 can be implemented by one or more computing device(s), such as computing device(s) 106, 107. In addition, FIG. 8 depicts steps performed in a particular order for purposes of illustration and discussion. The steps of any of the methods discussed herein can be adapted, rearranged, expanded, omitted, or modified in various ways without deviating from the scope of the present disclosure.

At (802), method 800 can include obtaining information indicative of the location of imaging platform 102. For instance, computing device(s) 107 can be configured to obtain a first set of information 110 associated with one or more location(s) of imaging platform 102. At (804), method 800 can include obtaining information indicative of the location of solar source 103. For instance, computing device(s) 107 can be configured to obtain a second set of information 111 associated with one or more location(s) of solar source 103. As described herein, the first and second sets of information 110, 111 can include data associated with global position systems, speed, orbit, etc. Computing device(s) 107 can be configured to obtain the first and/or second sets of information 110, 111 from one or more remote database(s) 108.

At (806), method 800 can include determining one or more image capture condition(s). The image capture condition(s) can include, for instance, location information associated with region of interest 105 and/or target object 101. Additionally, and/or alternatively, computing device(s) 106 can determine one or more positional range(s) of imaging platform 102 relative to solar source 103 based, at least in part, on the first and second sets of information 110, 111. The positional range(s) can be indicative of one or more position(s) at which imaging platform 102 is to obtain data indicative of one or more image frame(s) depicting, at least a portion of, target object 101. Moreover, the one or more positional range(s) (e.g., 204, 305) can be associated with one or more positions of the solar source 103 at which radiation from solar source 103 causes a higher level of reflectance with target object 101, than with a surrounding of target object 101 by creating a specular reflection.

For example, the positional range(s) can include first range 204 associated with elevation angle 201 of imaging platform 102 and/or second range 305 associated with azimuth angle 302 of imaging platform 102. In some implementations, first range 204 can include one or more elevation angle(s) 201 of imaging platform 102 that are substantially similar to elevation angle 203 of solar source 103. First range 204 can include one or more elevation angle(s) 201 of imaging platform 102 that are within +/−5 degrees of elevation angle 203 of solar source 103 and second range 305 can include one or more azimuth angle(s) 302 of imaging platform 102 that are within 165 degrees to 195 degrees of azimuth angle 304 of solar source 103, as described herein with reference to FIGS. 2 and 3. First and second range(s) 204, 305 can be associated with one or more position(s) of imaging platform 102 and/or solar source 103 at which radiation (e.g., light) from solar source 103 causes a higher level of reflectance with target object 101 than its surroundings (and/or one or more portions of region of interest 105) by creating a specular reflection. In some implementations, the computing device(s) 107 can determine time range 112 in which imaging platform 102 is within the one or more positional range(s) (e.g., 204, 305) of imaging platform 102 relative to solar source 103, as described above.

At (808), method 800 can include sending data indicative of the image capture condition(s). Computing device(s) 107 can send, to imaging platform 102, a first set of data 109 that is indicative of, for example, the one or more positional range(s) (e.g., 204, 305) such that imaging platform 102 can obtain a second set of data 113 indicative of a plurality of image frames when imaging platform 102 is within the positional range(s) (e.g., 204, 305). The first set of data 109 can also, and/or alternatively, be indicative of the location information associated with region of interest 105 and/or target object 101 and/or time range 112.

At (810), method 800 can include receiving the data indicative of the image capture condition(s). For instance, computing device(s) 106 of imaging platform 102 can receive the first set of data 109 indicative of the positional range(s) (e.g., 204, 305), the location information associated with region of interest 105 and/or target object 101, and/or time range 112. By way of example, in the event that imaging platform 102 is included on a satellite orbiting the earth, computing device(s) 106 can receive the first set of data from one or more ground station(s) (e.g., associated with computing device(s) 107) distributed globally.

At (812), method 800 can include determining whether a position of imaging platform 102 is within the one or more positional range(s) (e.g., 204, 305). For instance, computing device(s) 106 of imaging platform 102 can determine whether a position of imaging platform 102 is within first range 204 associated with elevation angle 201 of imaging platform 102 and second range 305 associated with azimuth angle 302 of imaging platform 102. Additionally, and/or alternatively, imaging platform 102 can determine it is within the positional range(s) (e.g., 204, 305) by using a clock device, as described above.

By way of example, elevation angle 203 of solar source 103 can be 45 degrees relative to horizontal plane 202, and first range 204 can include the elevation angles 201 from 40 to 50 degrees relative to horizontal plane 202. Azimuth angle 304 of solar source 103 can be 135 degrees relative to reference vector 303, and second range 305 can include the azimuth angles 302 from 300 to 330 degrees relative to reference vector 303. If elevation angle 201 is 47 degrees relative to horizontal plane 202, and azimuth angle 302 is 315 degrees relative to reference vector 303, then imaging platform 102 can determine that it is within the one or more positional range(s) (e.g., 204, 305).

Additionally, and/or alternatively, method 800 can include determining, by computing system 104, whether a position of imaging platform 102 is within the one or more positional range(s) (e.g., 204, 305). For instance, computing device(s) 107 can determine whether a position of imaging platform 102 is within the one or more positional ranges (204, 305). For example, computing device(s) 107 can determine whether imaging platform is oriented to capture image frame(s) of region of interest 105 and/or target object 101 based, at least in part, on the location information associated with region of interest 105 and/or target object 101. Computing device(s) 107 can determine whether a position of imaging platform 102 is within the one or more positional range(s) (e.g., 204, 305). Computing device(s) 107 can determine whether a time associated with imaging platform 102 is within time range 112.

At (814), method 800 can include obtaining data indicative of a plurality of image frames. For instance, computing device(s) 106 of imaging platform 102 can obtain a second set of data 113 that is indicative of a plurality of image frames, as described above. One or more of the image frames can be captured based, at least in part, on the one or more positional range(s) (e.g., 204, 305). For example, imaging platform 102 can use the location information associated with region of interest 105 (e.g., a black asphalt parking lot) and/or target object 101 (e.g., a black automobile) to orient its sensors in a manner such that it can capture image frames including, at least a portion of, region of interest 105 and/or target object 101. When imaging platform 102 determines that it is within the first and second ranges 204, 305 (e.g., such that the black automobile is experiencing a specular reflection due to solar source 103), imaging platform 102 can obtain second set of data 113 indicative of a plurality of image frames. Each image frame can include, at least a portion of, region of interest 105 (e.g., the black asphalt parking lot). One or more of the image frames can depict, at least a portion of, target object 101 (e.g., a black automobile). The portion of the target object 101 depicted in one or more of the image frame(s) may be associated with the specular reflection, while other portions of the region of interest may not.

Additionally, and/or alternatively, method 800 can include sending, to imaging platform 102, one or more command signal(s) to obtain second set of data 113 indicative of the one or more image frame(s). For instance, computing device(s) 107 can send, to imaging platform 102, one or more command signal(s) to obtain second set of data 113 indicative of the one or more image frame(s) when imaging platform 102 is within the one or more positional ranges (e.g., 204, 305). For example, computing device(s) 107 can determine that imaging platform 102 is within the first and second ranges 204, 305 (e.g., such that the black automobile is experiencing a specular reflection due to solar source 103) and computing device(s) 107 can send one or more command signal(s) to imaging platform 102 to obtain second set of data 113 indicative of one or more image frame(s).

Imaging platform 102 can receive the one or more command signal(s) and can obtain second set of data 113 indicative of one or more image frame(s). One or more of the image frame(s) can depict, at least a portion of, target object 101. The portion of target object 101 depicted in one or more of the image frame(s) may be associated with a specular reflection (while its surroundings and/or one or more other portion(s) of region of interest 105 may not).

At (816), method 800 can include sending data indicative of one of more image frames. For instance, computing device(s) 106 of imaging platform 102 can send a third set of data 114 that is indicative of one or more image frame(s) that depict, at least a portion of, target object 101. In some implementations, computing device(s) 106 of imaging platform 102 can send third set of data 114 to computing device(s) 107 via one or more radio frequency transmission signals.

At (818), method 800 can include receiving data indicative of one or more image frame(s). For instance, computing device(s) 107 of computing system 104 can receive third set of data 114 indicative of one or more image frame(s) that depict, at least a portion of, target object 101. As described above, the one or more image frame(s) can be captured based, at least in part, on the one or more positional range(s) (e.g., 204, 305).

At (820), method 800 can include coordinating the processing of one or more image frame(s). For instance, computing device(s) 107 can coordinate the processing of one or more image frame(s) that depict, at least a portion of, region of interest 105 and/or target object 101. As described herein, the one or more image frames can be reconstructed to create an image that includes, at least a portion of, target object 101. The image can be processed to identify target object 101 based, at least in part, on the specular reflection (e.g., glint) associated with target object 101.

In one example, target object 101 can be a black automobile included in region of interest 105, for example, a black asphalt parking lot. The processing techniques can include examining an image of the black automobile in the black asphalt parking lot to find a glint or glare produced from the black automobile as it experiences a specular reflection. If the portion of the image has a level of brightness and/or reflectance that is above a threshold (as described herein), the black automobile can be distinguished from the black asphalt parking lot in which it is located.

Figure 9:
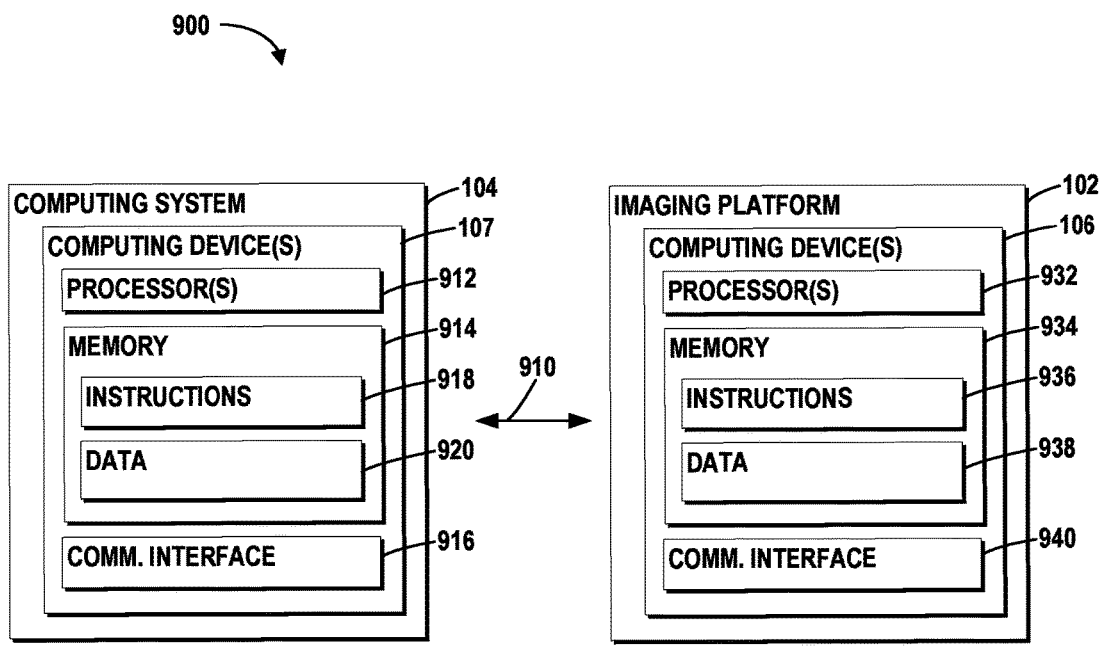
FIG. 9 depicts an example system according to example embodiments of the present disclosure.

FIG. 9 depicts an example computing system 900 that can be used to implement the methods and systems according to example aspects of the present disclosure. The system 900 can include computing system 104 and imaging platform 102, which can communicate with one another using signals 910 (e.g., radio frequency transmissions). The signals 910 can include, for instance, one or more command signals and/or one or more sets of data, as described herein. The system 900 can be implemented using a client-server architecture and/or other suitable architectures.

Computing system 104 can be associated with a control system for providing control commands to imaging platform 102. Computing system 104 can include one or more computing device(s) 107. Computing device(s) 107 can include one or more processor(s) 912 and one or more memory device(s) 914. Computing device(s) 107 can also include a communication interface 916 used to communicate with imaging platform 102. Communication interface 916 can include any suitable components for communicating with imaging platform 102, including for example, transmitters, receivers, ports, controllers, antennas, or other suitable components.

Processor(s) 912 can include any suitable processing device, such as a microprocessor, microcontroller, integrated circuit, logic device, or other suitable processing device. Memory device(s) 914 can include one or more computer-readable media, including, but not limited to, non-transitory computer-readable media, RAM, ROM, hard drives, flash drives, or other memory devices. Memory device(s) 914 can store information accessible by processor(s) 912, including computer-readable instructions 918 that can be executed by processor(s) 912. Instructions 918 can be any set of instructions that when executed by processor(s) 912, cause one or more processor(s) 912 to perform operations. For instance, execution of instructions 918 can cause processor(s) 912 to perform any of the operations and/or functions for which computing device(s) 107 are configured. In some implementations, execution of instructions 918 can cause processor(s) 912 to perform, at least a portion of, method 800 of enhancing object feature visibility for overhead imaging according to example embodiments of the present disclosure.

As shown in FIG. 9, memory device(s) 914 can also store data 920 that can be retrieved, manipulated, created, or stored by processor(s) 912. Data 920 can include, for instance, information associated with one or more location(s) of imaging platform 102 and/or solar source 103, data indicative of image capture condition(s), data indicative of one or more positional range(s) (e.g., 204, 305), data indicative of time range 112, the location information associated with region of interest 105 and/or target object 101, data indicative of one or more image frame(s), and/or any other data and/or information described herein. Data 920 can be stored in one or more database(s). The one or more database(s) can be connected to computing device(s) 107 by a high bandwidth LAN or WAN, or can also be connected to computing device(s) 107 through various other suitable networks. The one or more databases can be split up so that they are located in multiple locales.

Computing system 104 can exchange data with imaging platform 102 using signals 910. Although one imaging platform 102 is illustrated in FIG. 9, any number of imaging platforms can be configured to communicate with the computing system 104. In some implementations, imaging platform 102 can be associated with any suitable type of satellite system, including satellites, mini-satellites, micro-satellites, nano-satellites, etc. In some implementations, imaging platform 102 can be associated with an aircraft or other imaging platform such as a helicopter, an unmanned aerial vehicle, a drone, a balloon, or other suitable device.

Imaging platform 102 can include computing device(s) 106, which can include one or more processor(s) 932 and one or more memory device(s) 934. Processor(s) 932 can include one or more central processing units (CPUs). Memory device(s) 934 can include one or more computer-readable media and can store information accessible by processor(s) 932, including instructions 936 that can be executed by processor(s) 932. For instance, memory device(s) 934 can store instructions 936 for implementing an image collector and a data transmitter configured to capture a plurality of image frames and to transmit the plurality of image frames to a remote computing device (e.g., computing system 104). In some implementations, execution of instructions 936 can cause processor(s) 932 to perform any of the operations and/or functions for which imaging platform 102 is configured. In some implementations, execution of instructions 936 can cause processor(s) 932 to perform, at least a portion of, method 800 of enhancing object feature visibility for overhead imaging.

Memory device(s) 934 can also store data 938 that can be retrieved, manipulated, created, or stored by processor(s) 932. Data 938 can include, for instance, information associated with one or more location(s) of imaging platform 102 and/or solar source 103, data indicative of image capture condition(s), data indicative of one or more positional range(s) (e.g., 204, 305), data indicative of time range 112, location information associated with region of interest 105 and/or target object 101, data indicative of one or more image frame(s), and/or any other data and/or information described herein. Data 938 can be stored in one or more database(s). The one or more database(s) can be connected to computing device(s) 106 by a high bandwidth LAN or WAN, or can also be connected to computing device(s) 106 through various other suitable networks. The one or more database(s) can be split up so that they are located in multiple locales.

Imaging platform 102 can also include a communication interface 940 used to communicate with one or more remote computing device(s) (e.g., computing system 104, remote databases 108) using signals 910. Communication interface 940 can include any suitable components for interfacing with one or more remote computing device(s), including for example, transmitters, receivers, ports, controllers, antennas, or other suitable components.

In some implementations, one or more aspect(s) of communication among imaging platform 102, computing system 104, and/or remote databases(s) 108 can involve communication through a network. In such implementations, the network can be any type of communications network, such as a local area network (e.g. intranet), wide area network (e.g. Internet), cellular network, or some combination thereof. The network can also include a direct connection, for instance, between one or more of imaging platform 102, computing system 104, and/or remote databases 108. In general, communication through the network can be carried via a network interface using any type of wired and/or wireless connection, using a variety of communication protocols (e.g. TCP/IP, HTTP, SMTP, FTP), encodings or formats (e.g. HTML, XML), and/or protection schemes (e.g. VPN, secure HTTP, SSL).

The technology discussed herein makes reference to servers, databases, software applications, and other computer-based systems, as well as actions taken and information sent to and from such systems. One of ordinary skill in the art will recognize that the inherent flexibility of computer-based systems allows for a great variety of possible configurations, combinations, and divisions of tasks and functionality between and among components. For instance, server processes discussed herein can be implemented using a single server or multiple servers working in combination. Databases and applications can be implemented on a single system or distributed across multiple systems. Distributed components can operate sequentially or in parallel.

Furthermore, computing tasks discussed herein as being performed at a server can instead be performed at a user device. Likewise, computing tasks discussed herein as being performed at the user device can instead be performed at the server.

While the present subject matter has been described in detail with respect to specific example embodiments and methods thereof, it will be appreciated that those skilled in the art, upon attaining an understanding of the foregoing can readily produce alterations to, variations of, and equivalents to such embodiments. Accordingly, the scope of the present disclosure is by way of example rather than by way of limitation, and the subject disclosure does not preclude inclusion of such modifications, variations and/or additions to the present subject matter as would be readily apparent to one of ordinary skill in the art.

What is claimed is:

1. A computing system for enhancing object feature visibility for overhead imaging, comprising:
one or more processors; and
one or more memory devices, the one or more memory devices storing computer-readable instructions that when executed by the one or more processors cause the one or more processors to perform operations, the operations comprising:
obtaining a first set of information associated with one or more locations of an imaging platform;
obtaining a second set of information associated with one or more locations of a solar source;
determining one or more image capture conditions indicative of one or more constraints of the imaging platform while the imaging platform obtains one or more image frames, wherein the image capture conditions are indicative of one or more positional ranges of the imaging platform relative to the solar source based at least in part on the first and second sets of information, wherein the one or more positional ranges are indicative of one or more positions at which the imaging platform is to obtain the one or more image frames depicting at least a portion of a target object,
the one or more positional ranges are associated with one or more positions of the solar source at which radiation from the solar source causes a higher level of reflectance with the target object than with a surrounding of the target object;
sending, to the imaging platform, a first set of data indicative of the one or more positional ranges, wherein the imaging platform is configured to obtain a second set of data indicative of the one or more image frames depicting at least a portion of the target object based at least in part on the one or more positional ranges; and
receiving, from the imaging platform, a third set of data indicative of one or more of the image frames depicting at least a portion of the target object, wherein the one or more image frames were captured based at least in part on the one or more positional ranges.

2. The computing system of claim 1, wherein the one or more positional ranges comprise a first range associated with an elevation angle of the imaging platform and a second range associated with an azimuth angle of the imaging platform.

3. The computing system of claim 2, wherein the first range comprises one or more elevation angles of the imaging platform that are within +/−5 degrees of the elevation angle of the solar source.

4. The computing system of claim 2, wherein the second range comprises one or more azimuth angles of the imaging platform that are within 165 degrees to 195 degrees of the azimuth angle of the solar source.

5. The computing system of claim 1, wherein the imaging platform is further configured to determine whether a position of the imaging platform is within the one or more positional ranges.

6. The computer-implemented method of claim 1, wherein the target object is at least one of an automobile, a shipping container, or an amount of coal.

7. The computer-implemented method of claim 1, wherein the imaging platform is included on a satellite.

8. A computer-implemented method of enhancing object feature visibility for overhead imaging, the method comprising:
obtaining, by one or more computing devices, a first set of information associated with one or more locations of an imaging platform and a second set of information associated with one or more locations of a solar source;
determining, by the one or more computing devices, one or more image capture conditions indicative of one or more constraints of the imaging platform while the imaging platform obtains one or more image frames, wherein the image capture conditions are indicative of one or more positional ranges of the imaging platform relative to the solar source based, at least in part, on the first and second sets of information, wherein the one or more positional ranges are indicative of one or more positions at which the imaging platform is to obtain data indicative of the one or more image frames depicting at least a portion of a target object;
sending, to the imaging platform, a first set of data that is indicative of the one or more positional ranges such that the imaging platform can obtain a second set of data indicative of the one or more image frames when the imaging platform is within the one or more positional ranges; and
receiving, from the imaging platform, a third set of data indicative of one or more of the image frames depicting at least a portion of the target object, wherein the one or more image frames were captured based at least in part on the one or more positional ranges.

9. The computer-implemented method of claim 8, wherein the one or more positional ranges are associated with one or more positions of the solar source at which radiation from the solar source causes a higher level of reflectance with the target object than with a surrounding of the target object, and
wherein the portion of the target object depicted in one or more of the image frames is associated with the higher level of reflectance than other portions of the image frames.

10. The computer-implemented method of claim 8, wherein the one or more positional ranges comprise a first range associated with an elevation angle of the imaging platform and a second range associated with an azimuth angle of the imaging platform.

11. The computer-implemented method of claim 10, wherein the first range comprises one or more elevation angles of the imaging platform that are substantially similar to an elevation angle of the solar source.

12. The computer-implemented method of claim 10, wherein the first range comprises one or more elevation angles of the imaging platform that are within +/−5 degrees of the elevation angle of the solar source.

13. The computer-implemented method of claim 10, wherein the second range comprises one or more azimuth angles of the imaging platform that are within 165 degrees to 195 degrees of the azimuth angle of the solar source.

14. An imaging platform, comprising:
one or more processors; and
one or more memory devices, the one or more memory devices storing computer-readable instructions that when executed by the one or more processors cause the one or more processors to perform operations, the operations comprising:
receiving a first set of data indicative of one or more image capture conditions indicative of one or more constraints for the imaging platform to follow while the imaging platform obtains a plurality of image frames, wherein the one or more image capture conditions are indicative of one or more positional ranges of the imaging platform relative to a solar source,
the one or more positional ranges are associated with one or more positions of the solar source at which radiation from the solar source causes a higher level of reflectance with a target object than with at least one other portion of a region of interest that includes the target object;
determining whether a position of the imaging platform is within the one or more positional ranges;
obtaining a second set of data indicative of the plurality of image frames when the imaging platform is within the one or more positional ranges, wherein each image frame depicts at least a portion of the region of interest, and wherein one or more of the image frames depict at least a portion of the target object in the region of interest; and
sending, to one or more computing devices, a third set of data indicative of at least the one or more image frames that depict at least the portion of the target object.

15. The imaging platform of claim 14, wherein the one or more positional ranges of the imaging platform relative to the solar source comprise a first range associated with an elevation angle of the imaging platform and a second range associated with an azimuth angle of the imaging platform.

16. The imaging platform of claim 15, wherein the first range comprises one or more elevation angles of the imaging platform that are within +/−5 degrees of the elevation angle of the solar source.

17. The imaging platform of claim 16, wherein the second range comprises one or more azimuth angles of the imaging platform that are within 165 degrees to 195 degrees of the azimuth angle of the solar source.

18. The imaging platform of claim 14, wherein the first set of data is further indicative of a time range in which the imaging platform is within the one or more positional ranges of the imaging platform relative to the solar source, and wherein determining whether the position of the imaging platform is within the one or more positional ranges comprises:
determining whether a time associated with the imaging platform is within the time range.

19. The imaging platform of claim 18, wherein the time range comprises a first time that is indicative of when the position of the imaging platform will enter a first range associated with an elevation angle of the imaging platform and a second range associated with an azimuth angle of the imaging platform, and a second time that is indicative of when the position of the imaging platform will exit at least one of the first range associated with the elevation angle of the imaging platform or the second range associated with the azimuth angle of the imaging platform.

20. The imaging platform of claim 14, wherein the portion of the target object is associated with the higher level of reflectance than all other portions of the region of interest.

* * * * *